United States Patent [19]

Fuller

[11] Patent Number: 5,589,161
[45] Date of Patent: Dec. 31, 1996

[54] PIGMENTATION ENHANCER AND METHOD

[75] Inventor: Bryan B. Fuller, Edmond, Okla.

[73] Assignee: The Board of Regents of the University Oklahoma, Norman, Okla.

[21] Appl. No.: 302,153

[22] Filed: Sep. 8, 1994

Related U.S. Application Data

[63] Continuation of Ser. No. 943,998, Sep. 11, 1992, which is a continuation of Ser. No. 451,420, Dec. 15, 1989.

[51] Int. Cl.$^6$ .............................. A61K 7/42; A61K 7/40
[52] U.S. Cl. .................................. 424/59; 424/60; 424/63
[58] Field of Search .................................. 424/59, 60, 63

[56] References Cited

U.S. PATENT DOCUMENTS

| | | | |
|---|---|---|---|
| 2,418,695 | 4/1947 | Brown | 424/59 |
| 5,075,102 | 12/1991 | Habaud et al. | 424/59 |

FOREIGN PATENT DOCUMENTS

| | | | |
|---|---|---|---|
| 2064768 | 2/1991 | Canada | 424/59 |
| 2213376 | 8/1989 | France | 424/59 |
| 2620024 | 10/1989 | France | 424/59 |
| 62-45527 | 2/1987 | Japan | 424/59 |
| 8909258 | 10/1989 | WIPO | 424/59 |
| 9107945 | 6/1991 | WIPO | 424/59 |

OTHER PUBLICATIONS

Sagarin, *Cosmetics Science and Technologies*, 1957, pp. 189–200.

Kitano, Yukio, "Effects of Dibutyryl Adenosine 3', 5'–Cyclic Monophosphate on Human Melanocytes in Vitro", *Acta Dermatovener* (Stockholm), 56: 223–228 (1976).

Kitano, Yukio, "Effects of Melanocyte Stimulating Hormone Theophylline on Human Melanocytes in Vitro", *Arch. Derm. Res.*, 255: 163–168 (176).

Fuller et al., "Decay of Hormone Responsiveness in Mouse Melanoma Cells in Culture as a Function of Cell Density", *Journal of Cellular Physiology*, 103: 279–287 (1980).

Borovicka et al., "Skin protecting preparation against UV radiation", *Chemical Abstracts*, vol. 92, No. 12, Mar. 12, 1980, Columbus, Ohio, U.S.; Abstract No. 99450.

Fuller et al., "Endocrine Responsiveness in Human Melanocytes and Melanoma Cells in Culture", *JNCI*, 66(5): 799–802 (1981).

Sheridan et al., "Tritiated–Thymidine–Induced Increased DNA Content and Irreversible Differentiation in a Human Melanoma Cell Line", *Br. J. Exp. Path.*, 62:289–295 (1981).

Hadley et al., "Topical Application of a Melanotropic Peptide Induces Systemic Follicular Melanogenesis", *Life Sciences*, 40: 1889–1895 (1987).

Some commercial sun–tanning products which contain tyrosine are "Tan Magnifier" and 'Tropical Blend' by Schering/Plough; 'Hawaiian Tropic' by Tanning Research Labs; Estee Lauder suntan products; and 'Pre–tanning Accelerator' by Tanz.

Primary Examiner—Shelly A. Dodson
Attorney, Agent, or Firm—Dunlap & Codding, P.C.

[57] ABSTRACT

A composition for increasing synthesis of melanin in a human melanocyte thereby enhancing pigmentation of the human skin. Use of this composition promotes tanning of the human skin and increases photoprotection from ultraviolet radiation. An organ culture system comprising viable human foreskin samples which may be used to test the effects of agents on human skin, including pigmentation enhancers on human skin.

12 Claims, 1 Drawing Sheet

PIGMENTATION ENHANCER AND METHOD

RELATED REFERENCES

This is a continuation of U.S. Ser. No. 07/943,998, now allowed filed Sep. 11, 1992, which is a continuation of U.S. Ser. No. 07/451,420 filed on Dec. 15, 1989.

FIELD OF THE INVENTION

The present invention generally relates to compositions for topical application on a subject's skin, and specifically, to pigmentation enhancers, and to methods for assaying the effects of compositions on skin.

Summary of the Invention

The present invention comprises a composition of matter comprising an effective amount of a phosphodiesterase-inhibitor. The phosphodiesterase-inhibitor is capable of increasing levels of melanin in a human melanocyte. The composition also comprises an effective amount of a pharmaceutically acceptable topical carrier. The carrier is capable of delivering the phosphodiesterase-inhibitor to the melanocyte under in vivo conditions.

A composition of matter of the present invention may also comprise an effective amount of a methylxanthine which is capable of increasing levels of melanin in a human melanocyte. The composition also comprises an effective amount of a pharmaceutically acceptable topical carrier capable of delivering the methylxanthine to the melanocyte under in vivo conditions.

The present invention also comprises a method for at least partially shielding the skin from ultraviolet radiation in a subject. The subject's skin is treated with a pigment enhancer comprising an agent capable of increasing the amount of melanin in a human melanocyte, and a pharmaceutically acceptable topical carrier as previously described.

Another method of the present invention is a method of promoting tanning of a subject's skin. The skin is treated with a pigment enhancer as previously described.

The present invention is also directed to a human organ culture comprising a viable human foreskin tissue specimen having an epidermis and a dermis, a nutrient medium, and a means for supporting the foreskin in the medium. The foreskin is supported such that the dermis contacts the medium, and the epidermis is in substantially non-contacting relationship with the medium.

The human organ culture may be used to assay the effects of agents on skin. A baseline level of a biological factor in the foreskin is observed. The foreskin is contacted with the agent, and a post-contact observation made of the biological factor in the foreskin.

DETAILED DESCRIPTION OF THE PREFERRED EMBODIMENTS

Figure 1:
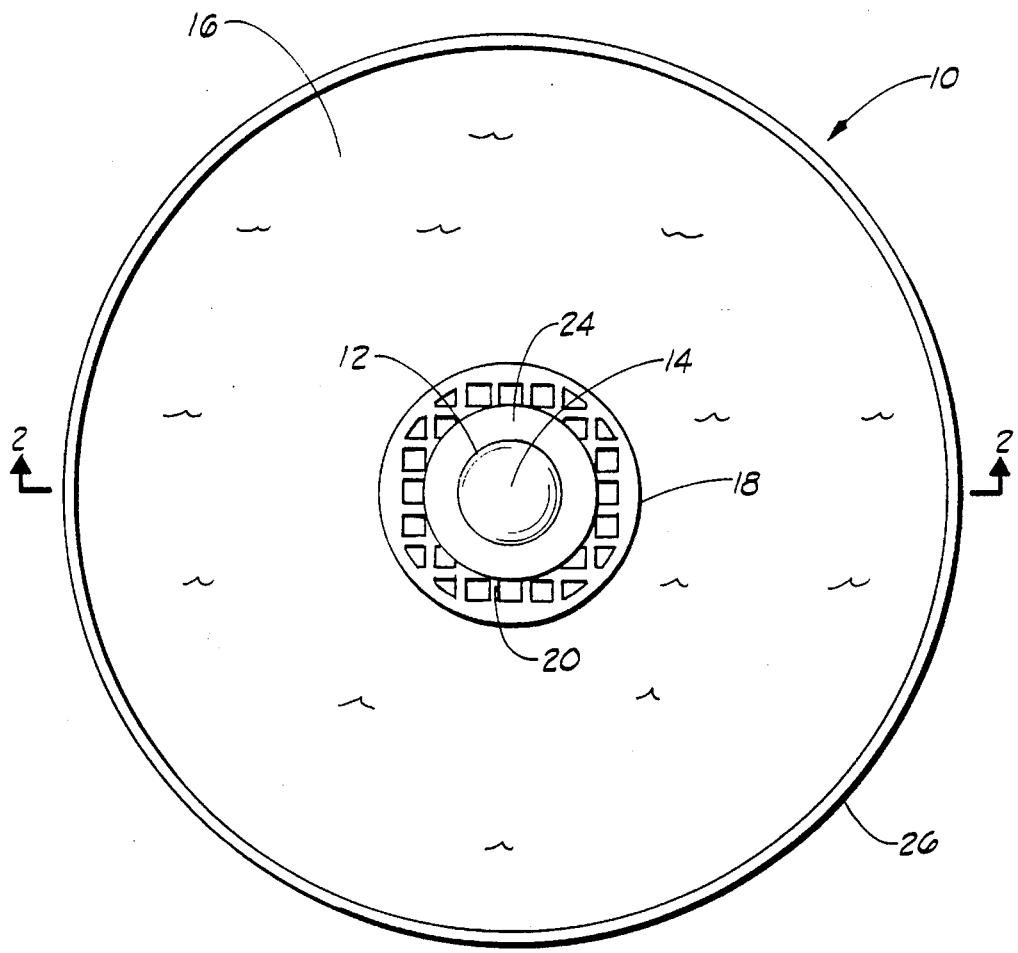
FIG. 1 is a plan view of the organ culture system of the present invention.

Skin color in humans arises from a complex series of cellular processes which are carried out within a unique population of cells called melanocytes. Melanocytes are located in the lower part of the epidermis, and their function is to synthesize a brown pigment, melanin, which protects the body from the damaging effects of ultraviolet radiation.

When skin is exposed to ultraviolet radiation, such as that contained in sunlight, melanocytes increase their synthesis of melanin. Melanin is deposited in melanosomes, which are vesicles found within the cell. The melanosomes are extruded from the cell and carried to the surface of the skin by keratinocytes, which internalize the melanin containing melanosomes. The end result is that the visible layers of the skin exhibit a brown color typically known as a "tan".

The darkness of the color observed in the skin is proportionate to the amount of melanin synthesized by melanocytes and transferred to the keratinocytes. By increasing melanogenesis, skin can be at least partially shielded from ultraviolet radiation, and tanning of the skin can be achieved without exposure of the skin to potentially damaging ultraviolet radiation. The present invention is directed to compositions and methods which increase melanogenesis in subjects. "Subjects" as used herein mean mammals, and, more preferably, humans.

The present invention comprises a composition of matter comprising an effective amount of an agent capable of increasing the amount of melanin in a melanocyte (hereafter "melanin-increasing agent") and, more preferably, in a human melanocyte. The melanin-increasing agent may function in any of the various ways that are believed to increase the amount of melanin: by increasing cAMP or derivatives of cAMP which function as cAMP in the melanocyte; by inhibiting phospho-diesterase; or by increasing tyrosinase activity. The melanin-increasing agent should be capable, alone or with the aid of a carrier as described hereafter, of crossing the melanocyte membrane, and more preferably, a human melanocyte membrane, in order to function as will be described.

Preferably, the melanin-increasing agent of the present invention comprises at least one phosphosdiesterase-inhibitor. Phosphodiesterase-inhibitors are believed to increase the amount of cAMP in biological systems. cAMP is believed to increase the activity of tyrosinase, which is the rate limiting enzyme which transforms the substrate tyrosine into melanin.

More preferably, the melanin-increasing agent of the present invention comprises at least one methylxanthine, and preferably a methylxanthine capable of functioning as a phosphodiesterase inhibitor. Most preferably, the agent comprises theophylline, isobutyl methylxanthine, or a derivative thereof such as aminophylline. Additionally, melanin-increasing agents of the present invention may be combined in order to enhance pigmentation of the individual.

The melanin-increasing agent may also comprise any pharmaceutically acceptable salt, analog, derivative or isomer of any phosphodiesterase inhibitor or any methylxanthine capable of functioning as described herein.

The composition of matter of the present invention additionally comprises an effective amount of a pharmaceutically acceptable topical carrier capable of delivering the agent to the melanocyte under in vivo conditions. The carrier may comprise any solution, suspension, emulsion or any other form which is capable of delivering the agent to the melanocyte under in vivo conditions. "Capable of delivery" as used herein, means that the carrier should permit the agent to cross the stratum corneum and successive cell layers found epidermal to the melanocyte, and/or aids the agent in crossing the melanocyte membrane. Furthermore, the carrier should not substantially interact with the agent so that the agent may perform its function as described herein.

The identity and quantity of the carrier will depend on the identity of the melanin-increasing agent used in the composition of the present invention. However, in many instances, the carrier will represent from about 95 percent to about 99 percent of the composition. In a preferred embodiment, the carrier may comprise 20% water, 50% isopropanol and 30% glycerol, combined with theophylline to produce a composition containing 0.2 percent by weight theophylline. In another embodiment, the carrier may comprise 50% propylene glycol, 20% water and 30% isopropanol to produce a composition containing 0.2 percent by weight theophylline.

The melanin-increasing agent is present in the composition of the present invention in any effective amount. An "effective amount" of the melanin-increasing agent is an amount which increases melanogenesis in the treated area of the subject. This amount may vary with, among other things, the identity of melanin-increasing agent and carrier, the subject's skin color and condition, and the degree of tanning and/or photoprotection sought. Preferably, the melanin-increasing agent is present in the composition from about 0.01 mM to about 100 mM. In a preferred embodiment, 18 mg of theophylline may be combined with 10 ml of a pharmaceutically acceptable topical carrier to cover about a 50 square inch area of skin. In another preferred embodiment, 180 mg of theophylline may be combined with 10 ml of a pharmaceutically acceptable topical carrier to form a composition capable of covering about a 50 square inch area of skin. In another embodiment, 2.2 mg of isobutyl methylxanthine may be combined with 10 ml of a pharmaceutically acceptable carrier to cover about a 50 square inch area of skin.

As previously discussed, the enzyme tyrosinase converts the substrate tyrosine into melanin. Since the composition of the present invention is believed to increase tyrosinase activity, the present invention preferably further comprises an effective amount of tyrosine so that the tyrosinase has as much substrate as possible to synthesize melanin. An "effective amount" of tyrosine means any amount which can be utilized by tyrosinase over the amount of tyrosine already present in the melanocyte. A preferable amount of tyrosine is about 0.01 mM to about 1 mM of the composition of the present invention. In a preferred embodiment, 1.8 mg of tyrosine may be combined with 18 mg of theophylline and 10 ml of a pharmaceutically acceptable topical carrier.

The composition of matter of the present invention is preferably applied directly to the skin of the individual seeking tanning of the skin and/or photoprotection from ultraviolet radiation. The treated area can be the entire skin surface of the subject or only those areas normally exposed to ultraviolet radiation. Since the composition of the present invention does not dye the skin, but rather permits the body chemistry to produce the tan, the tanning will not be streaked in the areas of application. Application of the composition may be repeated periodically for greater protection and/or tanning effect.

The composition of matter is preferably in a lotion or solution form which may be manually rubbed on the skin. Other means of application are acceptable such as aerosol sprays or the use of an applicator bottle.

ORGAN CULTURE SYSTEM

The adequate evaluation of the effects of an agent applied to human skin has been difficult, if not impossible, due to the nature of the systems previously used. For example, to study the pigmentation process, mouse melanoma cells, human melanoma cells, and human melanocytes in culture treated with tumor promotor agents have been used. The results of experiments using these abnormal cells were often inconsistent and did not always correlate to the results obtained in the normal human skin.

Rather than use abnormal cells placed outside their normal environment, the present invention comprises cells in situ in an organ and maintains the viability of the organ in order to emulate the human skin in vivo. It is the development of a human organ culture system of the present invention which has permitted the adequate evaluation and development of the compositions and methods of treatment of the present invention.

The human organ culture of the present invention employs a viable foreskin. "Viable" means there has been no substantial morphological change in the foreskin after surgical removal. Viability may be determined by changes in tissue ultrastructure determined through histochemical staining and/or dopa reaction staining, techniques which permit monitoring of any changes in the tissue ultrastructure.

The foreskins may be obtained by circumcising male neonates by standard surgical procedures. After surgical removal, the foreskin is preferably prepared for the organ culture by injection intradermally with the medium described hereafter. This swells the mucous membrane and allows for the removal of the membrane thereby allowing adequate nutrient flow to the foreskin through the dermis.

The foreskin comprises an epidermis which is normally exposed to the environment and a dermis opposing the epidermis. After surgical removal and preparation for the organ culture, the dermis, which is normally supplied nutrients by the body, is exposed to the environment. In order to maintain the viability of the foreskin, a nutrient medium supplies nutrients to the foreskin through the dermis as described hereafter.

The nutrient medium is any composition which maintains the viability of the foreskin. Preferably, the nutrient medium has a liquid phase such as a solution, suspension or emulsion. A portion of the medium may be obtained commercially, such as Iscove's modified Dulbecco's medium (IMDM), Ham's nutrient mixture F-10 medium, Minimum essential media (MEM), RPMI media 1630 or 1640, Dulbecco's Modified Eagle Media (D-MEM) or Media 199 all of which are manufactured by Gibco Laboratories of Grand Island, New York as well as other companies, the specification sheets of which are hereby incorporated by reference. Additionally the medium comprises about 10% to about 30% horse serum and about 2% to about 10% fetal bovine serum; the serums may be purchased from Hyclone Lab Inc., of Logan, Utah. If necessary, an alkalizer such as sodium bicarbonate may be added until the medium achieves a preferred pH, preferably about a physiological pH. Antibiotics such as penicillin and/or streptomycin may also be added for microbial control.

If transportation of the foreskin is necessary after surgical removal, the foreskin is immediately placed on an absorbent support saturated with the nutrient medium. In order to maintain the viability of the foreskin, the foreskin is disposed in the medium within about 3–4 hours after surgical removal. The position of the foreskin in the medium should be that the dermis contacts the medium and the epidermis is not substantially contacted by the medium.

Figure 2:
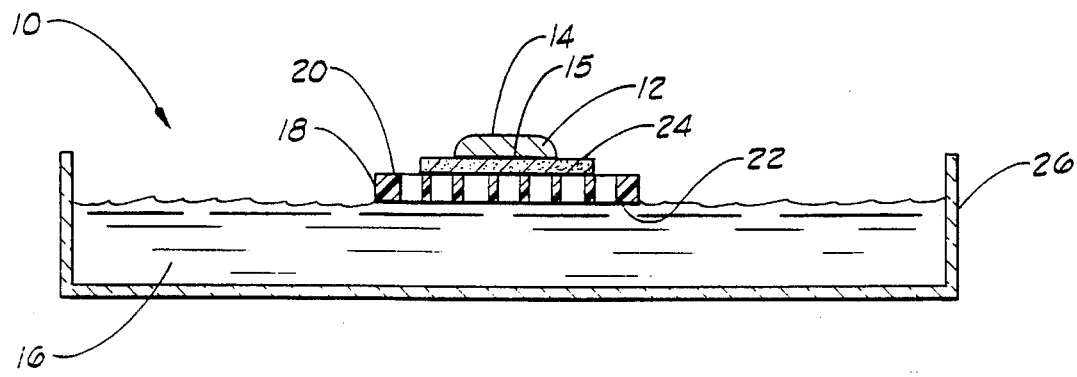
FIG. 2 is a side cross-section view of the organ culture system shown in FIG. 1 taken along line 2—2 shown in FIG. 1.

Referring to FIGS. 1 and 2 of the organ culture system 10, the present invention comprises a foreskin 12, having an epidermis 14 and a dermis 15. The foreskin 12 is placed in the medium 16 so that the medium 16 contacts the dermis 15 but does not substantially contact the epidermis 14. The epidermis 14 is in contact with the environment as under in vivo conditions. The medium 16 nourishes the foreskin 12, and maintains its viability while the organ culture is under study. About 7 days or less are generally needed to complete such a study.

The medium 16 comprises a liquid phase and is disposed in a container such as a petri dish 26. The amount of medium needed will depend upon, among other things, the container and the support means used. Generally about 5 ml to about 10 ml is a sufficient amount of medium for one foreskin in a petri dish having a diameter of 1.5 inches with the foreskin supported on a float as described hereafter.

The foreskin 12 may be supported by any means which will permit positioning of the foreskin in the medium 16 as previously described. Preferably, the foreskin 12 is disposed on a buoyant and permeable float 18 having a top 20 and a bottom 22; the dermis 15 contacts the top 20 of the float 18. The float 18 floats on top of the medium 16. The float 18 preferably comprises a sterile plastic screen such as a Swinnex 25 cm filter support screen manufactured by Millipore. More preferably, a permeable pad 24 is interposed between the dermis 15 and the top 20 of the float 18. The pad 24 functions to hold the foreskin 12 on the float 18. One example of a pad 24 used in accordance with the present invention is a AP20 025 00 filter manufactured by Millipore. Because both the float 18 and pad 24 are permeable to the culture medium 16, the medium maintains contact with the dermis 15 while the foreskin is positioned on the float 18, as required to maintain the foreskins viability. The float 18 is placed on top of the medium 16 and may freely move about the top of the medium 16.

Once the foreskin is disposed in the organ culture system as described herein, the organ culture system is incubated during the length of observation of the foreskin. Preferably the medium is changed daily, since nutrients may be depleted over time, and the incubation causes degradation of medium components.

In using the human organ culture system of the present invention, the foreskin is surgically removed, prepared and disposed in the organ culture system as described herein. Before positioning the foreskin in the system, the foreskin should be observed to determine the amount and/or the condition of the biological factor under study to obtain a baseline measurement.

After treatment of the foreskin with an agent, the biological factor is again observed for a post-treatment measurement to be compared to the baseline measurement. For example, if the amount of tyrosinase in the foreskin is under study, the amount of tyrosinase is determined as a baseline measurement prior to application of the agent to the foreskin. If the toxicity of an agent on skin is to be studied, the foreskin may be observed for DNA synthesis, protein synthesis, ATP synthesis, or any combination of these cell functions. If the permeability of an agent on skin is to be determined, the absence of the agent in the skin is the baseline measurement. Some examples of biological factors which may be studied are tyrosinase, melanin, DNA, RNA, proteins, carbohydrates, or any other factor that can be measured or observed for differences between the treated and the untreated foreskins.

If the foreskin is to be treated with an agent under study, the agent should be added to the medium 16, so that it comes into contact with the foreskin 12 through the medium 16. Alternatively, the agent can be placed directly on the epidermis 14. The treatment time will depend on the results sought, the identity of the agent under study, the time over which the foreskin can remain viable, and other variables.

After the foreskin has been treated with the agent under study, the foreskin may be observed and/or tested in any manner which will determine the differences in the foreskin from the observation and/or tests on the untreated foreskin. For example, the activity of tyrosinase may be measured as described herein and correlated to an increase in melanogenesis; the rate of DNA synthesis can be measured by $^3$H-thymidine uptake and compared to controls; or the increase or decrease in the synthesis of proteins and/or RNA can be measured by determining the rate of incorporation of [$^3$H] leucine (protein) or [$^3$H] uridine (RNA) into acid-precipitating material.

From the foregoing, it will be appreciated that the organ culture system of the present invention offers an opportunity to study the effects of many agents on human skin, and many biochemical processes of human skin. Factors other than pigmentation processes, and agents other than pigmentation enhancers may be evaluated for effects on the skin. For example, cosmetic agents or suspected toxic environmental compounds may be tested for their effects on skin morphology, DNA synthesis, abnormal chromosome appearance, skin cell viability, and protein and RNA synthesis. Also, the permeability of agents through the epidermis and the dermis may be studied in order to evaluate agents for use in transdermal delivery systems for systemic delivery of the agent.

The following examples illustrate the practice of the method and composition of the present invention:

Example 1

Preparation of Human Foreskin

At the time of surgical removal, human foreskins were placed on sterile gauze saturated with sterile IMDM medium (Iscove's modified Dulbecco's medium purchased from Irvine Scientific of Santa Ana, Calif.) for transportation from the Hospital nursery to the laboratory. The tissues were rinsed in sterile IMDM medium containing 500 U/ml penicillin and 500 µg/ml of streptomycin for 5 minutes. Under sterile conditions, an intradermal injection of medium was performed from the dermal side prior to dissection of the mucous membrane and lower dermis by scissors to make the thickness of skins equal. The foreskins were then cut into approximately 3 mm×3 mm squares and either frozen at −75° C. or placed in organ culture as described hereafter.

Example 2

Organ Culture

The organ culture medium was prepared from IMDM with glutamine supplemented with 20% horse serum, 5% fetal bovine serum, 100 U/ml penicillin, 100 µg/ml streptomycin and 3 mg/ml sodium bicarbonate. The serums were obtained from Hyclone Lab. Inc. of Logan Utah. Culture units were prepared by placing sterilized filters (AP20 025 00, Millipore) over sterilized support screens (25 cm Swinnex filter support screens, Millipore) in the wells of 6-well tissue culture plates (Falcon 3046) with medium added to the wells such that the skin support screens floated and the filter absorbed the medium from beneath. The tissue samples were placed, epidermis up, on top of the saturated filters and incubated at 37° C. in a 5% $CO_2$ humidified atmosphere. The medium was changed everyday. Harvested cultures were frozen at −75° C.

Example 3

Light Microscopy

For histological study, thawed samples of fresh tissue and explants were mounted in OCT compound (ICN Immuno Biologicals, Lisle, Illinois) and frozen by liquid nitrogen. Cryostat sections (6 μm thick) were fixed in 2% formaldehyde for 2 hours at 40° C., and then stained either with hematoxylin and eosin or subjected to dopa staining. The dopa reactions were carried out by incubation in two changes of 0.1% L-dopa solution buffered to pH 7.4 in 0.1 M sodium phosphate buffer for 4 hours at 37° C.

Example 4

Determination of Tyrosinase Activity

Tyrosinase activity in human skin organ cultures was determined by measuring the tyrosine hydroxylase activity of the enzyme. The assay measures the production of $^3H_2O$ during the conversion of [$^3H$]tyrosine to L-DOPA. Weighed skin preparations were incubated in 0.3 ml of a reaction mixture containing 0.01 mM of L-tyrosine, 5–6 uCi/ml of [$^3H$]tyrosine and 0.1 mM L-DOPA in 0.1 M of pH 6.8 phosphate buffer for 4 hours at 37° C. To terminate the reaction, 1 ml of phosphate buffer was added, the tubes vortexed, and 0.4 ml aliquots removed in triplicate and mixed with an equal volume of Norit SG activated charcoal (10% w/v, in 0.1N HCl). Following centrifugation at 2000 xg for 10 min, the supernatants (0.5 ml) were placed in scintillation vials, scintillation fluid added, and vials counted in a TM Analytic 6895 scintillation counter equipped with a DPM processor.

Example 5

Evaluation of Viability of the Human Foreskin

In order to assess the efficacy of the culture system, both black and white human foreskins were placed in culture and at 24 hours intervals skin sections were removed for histological examination by H&E staining and by dopa staining. The human foreskin retained its normal morphology throughout the 7 day length of the study. There was no difference in structural viability between black and white skin. When the dopa oxidase activity of cultured skin melanocytes was examined by dopa staining, a similar staining pattern between day 0 and day 7 foreskin cultures was observed, showing that the culture conditions maintain the viability of the skin for many days. Foreskins placed in culture within 3–4 hours of surgical removal showed normal structural integrity throughout the culture period whereas samples placed in culture more than 4 hours after removal did not maintain structural integrity.

When tyrosinase activity levels were determined in cultured skin, a marked decline in activity during the first 24 hours in culture in both black and white foreskins was observed. After this initial drop, however, tyrosinase activity stabilized for the remainder of the 7 day incubation period.

Example 6

Evaluation of Foreskin Treatment

Foreskins treated with α-MSH (melanocyte stimulating hormone from Sigma, St. Louis, Mo.) showed an increase in tyrosinase activity whereas foreskins treated with D-phe-MSH (Sigma, St. Louis, Mo.) showed a marked stimulation of tyrosinase. This shows that the organ culture system can respond to hormones.

A stronger stimulation of tyrosinase was found with theophylline. Human foreskins were treated with the compounds shown in Table 1, placed in culture, and incubated for 72 hours. The skins were then assayed for tyrosinase activity with the tyrosine hydroxylase assay method as described herein. As shown in Table 1, dibutyryl cAMP was less effective in stimulating tyrosinase activity.

Table 2 shows the activity of theophylline in a pharmaceutical topical carrier. Organ cultures were incubated with the compounds shown in Table 2 for 72 hours. The medium and compounds were changed daily. Tyrosinase activity was determined by measuring the tyrosine hydroxylase activity of the enzyme.

Human foreskin organ cultures were treated with the compounds listed in Table 3 for 3 days and tyrosinase activity determined as described herein. Theophylline was used at 1 mM.

TABLE 1

Summary of effects of hormones and other compounds on tyrosinase activity in human foreskin organ cultures.

| Treatment | Tyrosinase Activity | |
|---|---|---|
| | Stimulated | Unaffected |
| Theophylline (1 mM) | 11B(92%); 6W(86%) | 1B(8%); 1W(14%) |
| MSH (2 × $10^{-7}$ M) | 2B(33%); 2W(40%) | 4B(67%); 3W(60%) |
| dbcAMP (0.1 mM)[a] | 3B(33%); 1W(25%) | 6B(67%); 3W(75%) |
| D-phe-MSH ($10^{-8}$ M) | 2B(50%); 2W(50%) | 2B(50%); 2W(50%) |

[a]dbcAMP is dibutyryl cAMP. B = black; W = white;. Values are the averages of triplicate determinations ± s.d.

TABLE 2

Effect of IBMX (isobutyl methylxanthine) and theophylline in vehicle[a] on tyrosinase activity in human foreskin organ cultures.

| Treatment | Tyrosinase Activity pmoles $^3H_2O$/hour/mg skin |
|---|---|
| control | 3.15 ± 0.1 |
| IBMX (0.1 mM) | 7.03 ± 0.49 |
| Theophylline/vehicle (1 mM) | 6.32 ± 0.22 |

[a]vehicle consists of 20% water, 50% isopropanol and 30% glycerol. Values are the averages of triplicate assays ± s.d.

TABLE 3

Effect of Hormones and other compounds on tyrosinase activity in human foreskin organ cultures.

| Skin Type | Treatment | Tyrosinase Activity pmoles $^3H_2O$/hr/mg skin | Percentage of control |
|---|---|---|---|
| Black | control | 2.55 ± 0.13 | |
| | theophylline | 5.40 ± 0.26 | 212 |
| Black | control | 3.09 ± 0.12 | |

TABLE 3-continued

Effect of Hormones and other compounds on tyrosinase activity in human foreskin organ cultures.

| Skin Type | Treatment | Tyrosinase Activity pmoles $^3$H$_2$O/hr/mg skin | Percentage of control |
|---|---|---|---|
| | theophylline | 6.1 ± 0.24 | 197 |
| White | control | 0.31 ± 0.03 | |
| | theophylline | 0.95 ± 0.05 | 307 |
| | D-phe-MSH ($10^{-9}$ M) | 0.51 ± 0.05 | 165 |
| Hispanic | control | 0.41 ± 0.02 | |
| | D-phe-MSH ($10^{-8}$ M) | 1.43 ± 0.16 | 349 |
| | D-phe-MSH ($10^{-9}$ M) | 0.91 ± 0.03 | 222 |

Values are the averages of triplicate determinations ± s.d.

Changes may be made in the combination and arrangement of parts, elements, steps, compositions and procedures described herein without departing from the spirit and scope of the invention as defined in the following claims.

What is claimed is:

1. A composition of matter for stimulating melanogenesis in melanocytes of human epidermis, comprising:

an effective amount of a methylxanthine effective in increasing tyrosinase activity in the melanocytes to an amount sufficient to result in increasing levels of melanin in a human melanocyte in vivo; and an effective amount of a pharmaceutically acceptable topical carrier capable of delivering the methylxanthine to the melanocyte under in vivo conditions.

2. The composition of claim 1 in which the methylxanthine comprises at least one member of the group consisting of theophylline, isobutyl methylxanthine, aminophylline, and pharmaceutically acceptable salts of theophylline, aminophylline or isobutyl methylxanthine capable of increasing melanin in the human melanocyte.

3. The composition of claim 1 further comprising:

an effective amount of dibutyryl cAMP.

4. The composition of claim 1 in which the methylxanthine comprises from about 0.02 percent to about 2 percent by weight of the composition of matter.

5. The composition of claim 1 in which the methylxanthine comprises from about 0.1 mM to about 100 mM of the composition of matter.

6. A composition of matter for stimulating melanogenesis in melanocytes of human epidermis, comprising:

an effective amount of a theophylline effective in increasing tyrosinase activity in the melanocytes to an amount sufficient to result in increasing levels of melanin in a human melanocyte in vivo; and an effective amount of a pharmaceutically acceptable topical carrier capable of delivering the theophylline to the melanocyte under in vivo conditions.

7. A composition of matter for stimulating melanogenesis in melanocytes of human epidermis, comprising:

an effective amount of an isobutyl methylxanthine effective in increasing tyrosinase activity in the melanocytes to an amount sufficient to result in increasing levels of melanin in a human melanocyte in vivo; and an effective amount of a pharmaceutically acceptable topical carrier capable of delivering the isobutyl methylxanthine to the melanocyte under in vivo conditions.

8. A composition of matter for stimulating melanogenesis in melanocytes of human epidermis, comprising:

an effective amount of a methylxanthine effective in increasing tyrosinase activity in the melanocytes to an amount sufficient to result in increasing levels of melanin in a human melanocyte in vivo; and an effective amount of a pharmaceutically acceptable carrier comprising an alcohol, the carrier capable of delivering the methylxanthine to the melanocyte under in vivo conditions.

9. The composition of claim 8 in which the methylxanthine comprises at least one member of the group consisting of theophylline, isobutyl methylxanthine, aminophylline, and pharmaceutically acceptable salts of theophylline, aminophylline or isobutyl methylxanthine capable of increasing melanin in the human melanocyte.

10. The composition of claim 8 further comprising:

an effective amount of dibutyryl cAMP.

11. The composition of claim 8 in which the methylxanthine comprises from about 0.02 percent to about 2 percent by weight of the composition of matter.

12. The composition of claim 8 in which the methylxanthine comprises from about 0.1 mM to about 100 mM of the composition of matter.

* * * * *